(12) United States Patent
Youmans et al.

(10) Patent No.: US 8,273,015 B2
(45) Date of Patent: Sep. 25, 2012

(54) METHODS FOR IMAGING THE ANATOMY WITH AN ANATOMICALLY SECURED SCANNER ASSEMBLY

(75) Inventors: David C. Youmans, Loveland, OH (US); Jane A. Sheetz, Cincinnati, OH (US); Gary L. Long, Cincinnati, OH (US); Paul G. Ritchie, Loveland, OH (US); Michael S. Cropper, Edgewood, KY (US); Jere J. Brophy, Loveland, OH (US); Bradley E. White, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1145 days.

(21) Appl. No.: 11/749,188

(22) Filed: May 16, 2007

(65) Prior Publication Data
US 2008/0167546 A1 Jul. 10, 2008

(51) Int. Cl.
*A61B 1/06* (2006.01)
*G02B 6/06* (2006.01)

(52) U.S. Cl. .......................... 600/182; 600/160; 385/117

(58) Field of Classification Search .................. 600/182, 600/155, 166, 110, 101, 109, 113, 114, 173, 600/160, 129
See application file for complete search history.

(56) References Cited

U.S. PATENT DOCUMENTS

| | | | |
|---|---|---|---|
| 3,758,199 A | 9/1973 | Thaxter | |
| 3,959,582 A | 5/1976 | Law et al. | |
| 3,961,621 A * | 6/1976 | Northeved | 600/566 |
| 4,082,635 A | 4/1978 | Fritz et al. | |
| 4,141,362 A | 2/1979 | Wurster | |
| 4,313,431 A | 2/1982 | Frank | |
| 4,319,563 A * | 3/1982 | Kubota | 600/129 |
| 4,379,039 A | 4/1983 | Fujimoto et al. | |
| 4,403,273 A | 9/1983 | Nishioka | |
| 4,409,477 A | 10/1983 | Carl | |
| 4,421,382 A | 12/1983 | Doi et al. | |
| 4,524,761 A | 6/1985 | Hattori et al. | |
| 4,527,552 A | 7/1985 | Hattori | |
| 4,573,465 A | 3/1986 | Sugiyama et al. | |
| 4,576,999 A | 3/1986 | Eckberg | |
| 4,597,380 A | 7/1986 | Raif et al. | |
| 4,643,967 A | 2/1987 | Bryant | |
| 4,676,231 A | 6/1987 | Hisazumi et al. | |
| 4,760,840 A | 8/1988 | Fournier, Jr. et al. | |
| 4,803,550 A | 2/1989 | Yabe et al. | |

(Continued)

FOREIGN PATENT DOCUMENTS
DE 3837248 5/1990
(Continued)

OTHER PUBLICATIONS

Kiang, M-H et al., "Surface-Micromachined Electrostatic-Comb Driven Scanning Micromirrors for Barcode Scanners" (date of first publication unknown).

(Continued)

*Primary Examiner* — Philip R Smith
*Assistant Examiner* — William Chou

(57) ABSTRACT

A method for viewing a portion of a patient's anatomy that comprises placing a scanner assembly including an oscillating reflector in the anatomy, securing the scanner assembly to an anatomical structure, scanning the anatomy with the scanner assembly secured to the anatomical structure, collecting radiation returned from the scanned anatomy, and generating a displayable image of the anatomy.

2 Claims, 11 Drawing Sheets

U.S. PATENT DOCUMENTS

| | | | |
|---|---|---|---|
| 4,872,458 A | 10/1989 | Kanehira et al. |
| 4,902,083 A | 2/1990 | Wells |
| 4,902,115 A | 2/1990 | Takahashi |
| 4,934,773 A | 6/1990 | Becker |
| 4,938,205 A | 7/1990 | Nudelman |
| 5,003,300 A | 3/1991 | Wells |
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A | 5/1993 | Sinofsky |
| 5,218,195 A | 6/1993 | Hakamata |
| 5,251,025 A | 10/1993 | Cooper et al. |
| 5,251,613 A | 10/1993 | Adair |
| 5,269,289 A | 12/1993 | Takehana et al. |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,429,604 A * | 7/1995 | Hammersmark et al. .. 604/95.04 |
| 5,436,655 A | 7/1995 | Hiyama et al. |
| 5,467,104 A | 11/1995 | Furness, III et al. |
| 5,488,862 A | 2/1996 | Neukermans et al. |
| 5,531,740 A | 7/1996 | Black |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A | 3/1997 | Konno et al. |
| 5,629,790 A | 5/1997 | Neukermans et al. |
| 5,643,175 A | 7/1997 | Adair |
| 5,648,618 A | 7/1997 | Neukermans et al. |
| 5,649,952 A | 7/1997 | Lam |
| 5,653,677 A | 8/1997 | Okada et al. |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,011,889 A * | 1/2000 | Daniel et al. ................ 385/117 |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A | 5/2000 | Furusawa et al. |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 | 4/2001 | Lai |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,296,608 B1 * | 10/2001 | Daniels et al. ................ 600/104 |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,366,726 B1 * | 4/2002 | Wach et al. ................ 385/115 |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |

| Patent No. | Date | Name |
|---|---|---|
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 | 9/2002 | Knodel et al. |
| 6,462,770 B1 | 10/2002 | Cline et al. |
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart et al. |
| 6,492,962 B2 | 12/2002 | Melville et al. |
| 6,494,578 B1 | 12/2002 | Plummer et al. |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Katashiro et al. |
| 6,560,028 B2 | 5/2003 | Melville et al. |
| 6,563,105 B2 | 5/2003 | Seibel et al. |
| 6,563,106 B1 | 5/2003 | Bowers et al. |
| 6,572,606 B2 | 6/2003 | Kliewer et al. |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,632,171 B2 * | 10/2003 | Iddan et al. ............ 600/106 |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 * | 2/2004 | Kilcoyne et al. .......... 600/300 |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 | 9/2004 | Hoffman |
| 6,790,173 B2 * | 9/2004 | Saadat et al. ............ 600/114 |
| 6,795,221 B1 | 9/2004 | Urey |
| 6,802,809 B2 | 10/2004 | Okada |
| 6,803,561 B2 | 10/2004 | Dunfield |
| 6,814,699 B2 * | 11/2004 | Ross et al. ............ 600/179 |
| 6,821,245 B2 | 11/2004 | Cline et al. |
| 6,845,190 B1 | 1/2005 | Smithwick et al. |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 | 6/2005 | Swayze et al. |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel et al. |
| 6,976,994 B2 | 12/2005 | Ballou et al. |
| 6,978,921 B2 | 12/2005 | Shelton, IV et al. |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B1 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,242,833 B2 * | 7/2007 | Yang et al. ............ 385/117 |
| 7,271,383 B2 | 9/2007 | Chee |
| 7,391,013 B2 | 6/2008 | Johnston et al. |
| 7,530,948 B2 * | 5/2009 | Seibel et al. ............ 600/178 |
| 7,727,145 B2 * | 6/2010 | Yokoi et al. ............ 600/109 |
| 2001/0012429 A1 * | 8/2001 | Wach et al. ............ 385/115 |
| 2001/0055462 A1 | 12/2001 | Seibel |
| 2002/0015724 A1 | 2/2002 | Yang et al. |
| 2002/0024495 A1 | 2/2002 | Lippert et al. |
| 2002/0050956 A1 | 5/2002 | Gerhard et al. |
| 2002/0075284 A1 | 6/2002 | Rabb, III |
| 2002/0088925 A1 | 7/2002 | Nestorovic et al. |
| 2002/0115922 A1 | 8/2002 | Waner et al. |
| 2002/0141026 A1 | 10/2002 | Wiklof et al. |
| 2002/0158814 A1 | 10/2002 | Bright et al. |
| 2002/0163484 A1 | 11/2002 | Furness, III et al. |
| 2002/0167462 A1 | 11/2002 | Lewis et al. |
| 2002/0171776 A1 | 11/2002 | Tegreene et al. |
| 2002/0171937 A1 | 11/2002 | Tegreene et al. |
| 2003/0016187 A1 | 1/2003 | Melville et al. |
| 2003/0030753 A1 | 2/2003 | Kondo et al. |
| 2003/0032143 A1 | 2/2003 | Neff et al. |
| 2003/0034709 A1 | 2/2003 | Jerman |
| 2003/0058190 A1 | 3/2003 | Lewis et al. |
| 2003/0086172 A1 | 5/2003 | Urey |
| 2003/0092995 A1 | 5/2003 | Thompson |
| 2003/0130562 A1 | 7/2003 | Barbato et al. |
| 2003/0142934 A1 | 7/2003 | Pan et al. |
| 2003/0159447 A1 | 8/2003 | Sergio et al. |
| 2003/0208107 A1 * | 11/2003 | Refael ............ 600/300 |
| 2003/0214460 A1 | 11/2003 | Kovacs |
| 2003/0216729 A1 | 11/2003 | Marchitto et al. |
| 2004/0004585 A1 | 1/2004 | Brown et al. |
| 2004/0057103 A1 | 3/2004 | Bernstein |
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0118821 A1 | 6/2004 | Han et al. |
| 2004/0119004 A1 | 6/2004 | Wine et al. |
| 2004/0122328 A1 | 6/2004 | Wang et al. |
| 2004/0133786 A1 | 7/2004 | Tarbouriech |

| | | | |
|---|---|---|---|
| 2004/0151466 A1 | 8/2004 | Crossman-Bosworth et al. | |
| 2004/0155186 A1 | 8/2004 | Nestorovic et al. | |
| 2004/0155834 A1 | 8/2004 | Wit et al. | |
| 2004/0179254 A1 | 9/2004 | Lewis et al. | |
| 2004/0196518 A1 | 10/2004 | Wine et al. | |
| 2004/0223202 A1 | 11/2004 | Lippert et al. | |
| 2004/0225222 A1 | 11/2004 | Zeng et al. | |
| 2004/0236371 A1 | 11/2004 | McNally-Heintzelman et al. | |
| 2004/0240866 A1 | 12/2004 | Ramsbottom | |
| 2004/0252377 A1 | 12/2004 | Urey | |
| 2004/0254474 A1 | 12/2004 | Seibel et al. | |
| 2005/0010787 A1 | 1/2005 | Tarbouriech | |
| 2005/0014995 A1 | 1/2005 | Amundson et al. | |
| 2005/0020877 A1 | 1/2005 | Ishihara et al. | |
| 2005/0020926 A1 | 1/2005 | Wiklof et al. | |
| 2005/0023356 A1 | 2/2005 | Wiklof et al. | |
| 2005/0030305 A1 | 2/2005 | Brown et al. | |
| 2005/0038322 A1 | 2/2005 | Banik | |
| 2005/0116038 A1* | 6/2005 | Lewis et al. | 235/454 |
| 2005/0162762 A1 | 7/2005 | Novak | |
| 2005/0165272 A1* | 7/2005 | Okada et al. | 600/114 |
| 2005/0187441 A1 | 8/2005 | Kawasaki et al. | |
| 2005/0203343 A1 | 9/2005 | Kang et al. | |
| 2005/0215911 A1 | 9/2005 | Alfano et al. | |
| 2005/0240147 A1 | 10/2005 | Makower et al. | |
| 2005/0288555 A1* | 12/2005 | Binmoeller | 600/160 |
| 2006/0010985 A1 | 1/2006 | Schneider | |
| 2006/0084867 A1 | 4/2006 | Tremblay et al. | |
| 2006/0122522 A1* | 6/2006 | Chavan et al. | 600/505 |
| 2006/0164330 A1 | 7/2006 | Bright et al. | |
| 2006/0183246 A1 | 8/2006 | Wiesner et al. | |
| 2006/0195014 A1 | 8/2006 | Seibel et al. | |
| 2006/0238774 A1 | 10/2006 | Lindner et al. | |
| 2006/0245971 A1 | 11/2006 | Burns et al. | |
| 2006/0284790 A1 | 12/2006 | Tegreene et al. | |
| 2007/0032701 A1* | 2/2007 | Fowler et al. | 600/173 |
| 2007/0038119 A1 | 2/2007 | Chen et al. | |
| 2007/0046778 A1 | 3/2007 | Ishihara et al. | |
| 2007/0135770 A1 | 6/2007 | Hunt et al. | |
| 2007/0142714 A1* | 6/2007 | Shumate et al. | 600/300 |
| 2007/0156021 A1 | 7/2007 | Morse et al. | |
| 2007/0161876 A1 | 7/2007 | Bambot et al. | |
| 2007/0162093 A1 | 7/2007 | Porter et al. | |
| 2007/0167681 A1 | 7/2007 | Gill et al. | |
| 2007/0173686 A1* | 7/2007 | Lin et al. | 600/102 |
| 2007/0173707 A1 | 7/2007 | Mitra | |
| 2007/0179366 A1 | 8/2007 | Pewzner et al. | |
| 2007/0197865 A1 | 8/2007 | Miyake et al. | |
| 2007/0197874 A1 | 8/2007 | Ishihara | |
| 2007/0197875 A1 | 8/2007 | Osaka | |
| 2007/0203413 A1 | 8/2007 | Frangioni | |
| 2007/0213588 A1 | 9/2007 | Morishita et al. | |
| 2007/0213618 A1 | 9/2007 | Li et al. | |
| 2007/0225695 A1 | 9/2007 | Mayer et al. | |
| 2007/0238930 A1 | 10/2007 | Wiklof et al. | |
| 2007/0244365 A1 | 10/2007 | Wiklof | |
| 2007/0260121 A1 | 11/2007 | Bakos et al. | |
| 2007/0260273 A1 | 11/2007 | Cropper et al. | |
| 2008/0013960 A1* | 1/2008 | Tearney et al. | 398/139 |
| 2008/0058629 A1 | 3/2008 | Seibel et al. | |
| 2009/0005636 A1 | 1/2009 | Pang et al. | |
| 2009/0182202 A1* | 7/2009 | Vayser et al. | 600/182 |
| 2010/0056864 A1* | 3/2010 | Lee | 600/109 |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Lewis, J.R. et al., "Scanned beam medical imager," MOEMS Display and Imaging Systems II, Proceedings of SPIE vol. 5348, pp. 40-51 (2004).

James, R. et al., "Update on MEMS-based Scanned Beam Imager" (date of first publication unknown).

Wiklof, C., "Display technology spawns laser camera," Laser Focus World (Dec. 2004).

"Press Information—Phillips' Fluid Lenses Bring Things into Focus," http://www.newscenter.philips.com (Mar. 3, 2004).

Lettice, J., "The $5 'no moving parts' fluid zoom lens—twice," The Register (Mar. 15, 2004).

"Volcano Products—IVUS Imaging Visions® PV018," http://www.volcanotherapeutics.com (date of first publication unknown).

Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).

"Crystalplex Technology—PlxBead™ Superior Qualities," http://www.crystalplex.com (date of first publication unknown).

"Microvision [illuminating information] Products/Overview, Corporate Overview Presentation 2006" (2006).

"Holographic Beam Combiner for Ladar, Printer, Fiber Optics, and Cancer Treatment," by Digital Optics Technologies, Inc., http://www.mdatechnology.net (date of first publication unknown).

Brown, D.M., Abstract from SPIE Digital Library for "High-power laser diode beam combiner," Optical Engineering, vol. 42, Issue 11 (2003).

Literature entitled "All fiber beam combiner from Point Source" (Oct. 13, 2006).

"Custom Polarzing Cube Beamsplitters," from GlobalSpec The Engineering Search Engine, http://www.globalspec.com (date of first publication unknown).

Literature entitled "Dallas Semiconductor MAXIM—Visible-Laser Driver has Digitally Controlled Power Modulation," by Maxim Intergrated Products, http://www.maxim-ic.com (Jul. 1, 2001).

"Scan Mode Strategies for SCUBA-2" (May 25, 2005).

Seifert, M. et al., "High Power Diode Laser Beam Scanning in Multi-Kilowatt Range," Proceedings of the 23rd International Congress on Applications of Lasers and Electro-Optics (2004).

Jutzi, B. et al., "Sub-Pixel Edge Localization Based on Laser Waveform Analysis," ISPRS WG III/3, III/4, V/3 Workshop "Laser scanning 2005," Enschede, The Netherlands (Sep. 12-14, 2005).

"Bladeless Trocars," by Johnson & Johnson, http://www.jnjgateway.com (date of first publication unknown).

Yeh, R. et al., "Microelectromechanical Components for Articulated Microrobots" (date of first publication unknown).

Xu, Q. et al., "Micrometre-scale silicon electro-optic modulator," Nature, vol. 435, pp. 325-327 (May 19, 2005).

Park, H. et al., "Development of Double-Sided Silicon Strip Position Sensor," 2005 IEEE Nuclear Science Symposium Conference Record, pp. 781-785 (2005).

Hammond, S.W., "Architecture and Operation of a Systolic Sparse Matrix Engine," Proceedings of the 3rd SIAM Conference on Parallel Processing for Scientific Computing, pp. 419-423 (1987).

Ra, H. et al., "Biomedical Optics & Medical Imaging—Microtechnology enables endoscopic confocal microscopy," SPIE (http://spie.org) (2007).

Invitation to Pay Additional Fees with Partial International Search Report, PCT/US2008/074275 (Jan. 16, 2009).

Invitation to Pay Additional Fees with Partial International Search Report, PCT/US2008/074273 (Dec. 30, 2008).

International Search Report issued regarding International Application No. PCT/US2007/078868 (Mar. 28, 2008).

PCT, International Search Report, PCT/US2008/056589 (Jul. 30, 2008).

PCT, International Search Report, PCT/US2008/059231 (Jul. 4, 2008).

PCT, International Search Report, PCT/US2007/087923 (May 21, 2008).

PCT, International Search Report, PCT/US2008/056596 (Jun. 23, 2008).

PCT, International Search Report, PCT/US2008/059235 (Jul. 14, 2008).

PCT, International Search Report, PCT/US2007/087930 (Jul. 3, 2008).

PCT, International Search Report, PCT/US2008/051274 (Jul. 18, 2008).

PCT, International Search Report, PCT/US2008/066552 (Oct. 23, 2008).

US, Office Action, U.S. Appl. No. 11/651,255 (Apr. 5, 2011).

US, Office Action, U.S. Appl. No. 11/651,255 (Nov. 10, 2010).

US, Advisory Action, U.S. Appl. No. 11/651,255 (Jun. 14, 2011).

* cited by examiner

METHODS FOR IMAGING THE ANATOMY WITH AN ANATOMICALLY SECURED SCANNER ASSEMBLY

CROSS-REFERENCE TO RELATED APPLICATION

This application claims the benefit of and is a continuation-in-part of U.S. Nonprovisional application Ser. No. 11/651,255 filed Jan. 9, 2007, which is hereby incorporated by reference.

BACKGROUND

The present application relates generally to imaging the anatomy with a resonant scanner that has been secured to an anatomical structure.

U.S. Published application 2005/0020926 discloses a scanned beam imager that may be used in applications in which cameras have been used in the past. In particular it can be used in medical devices such as video endoscopes, laparoscopes, etc.

The scanned beam imager disclosed has an illuminator that creates a first beam of light and a scanner that deflects the first beam of light across a field-of-view (FOV). The scanned beam of light sequentially illuminates spots in the FOV corresponding to various beam positions. While the beam illuminates the spots, the illuminating light beam is reflected, absorbed, scattered, refracted, or otherwise affected by the object or material in the FOV to produce scattered light energy. A portion of the scattered light energy travels to detectors that receive the light and produce electrical signals corresponding to the amount of light energy received, which is then converted to separate electrical signals. The electrical signals pass to a controller that builds up a digital image and transmits it for further processing, decoding, archiving, printing, display, or other treatment or use.

Such scanned beam imagers are a useful tool for imaging, but may be useful for much more. In one embodiment the "imager" is more than just and imager, but is a scanner assembly that may be able to image, diagnose, analyze, treat, or activate a portion of the FOV or a substance within the FOV. The scanner assembly may be made on a smaller scale than typical cameras, deployable or incorporated into a medical instrument, and/or include zoom capabilities, which all make for a less invasive medical procedure. Less invasive medical procedures are easier for a patient to recover from. More specifically, a smaller scanner assembly will reduce the size of the incision or opening necessary to introduce the scanner assembly. The deployable scanner assembly itself or a medical instrument with the scanner assembly incorporated within its structure will reduce the number of instruments that need to be introduced into the body. Zoom capabilities allow the user to enlarge or reduce the image without moving the actual scanner assembly once inside the body.

BRIEF SUMMARY

In one aspect, the invention includes a method for viewing a portion of a patient's anatomy that comprises placing a scanner assembly including an oscillating reflector in the anatomy, securing the scanner assembly to an anatomical structure, scanning the anatomy with the scanner assembly secured to the anatomical structure, collecting radiation returned from the scanned anatomy, and generating a displayable image of the anatomy.

In another aspect, the invention includes a scanner assembly for use with a scanning beam device. The scanner assembly comprises a housing, an oscillating reflector to direct a beam of radiation onto a portion of a patient's anatomy, a cable extending from the housing to link the reflector to a component of a scanning beam device, and a connecting structure to secure the housing to an anatomical structure.

In another embodiment, the invention includes a scanner assembly and a collector that converts from a first conformation to facilitate insertion into the anatomy and a second conformation to facilitate imaging the anatomy that comprises a scanner assembly with a plurality of fiber bundles arranged around its periphery, the bundles being longitudinally staggered in the first conformation such that the combination of the bundles and the assembly provides a pointed end for inserting into the anatomy and in the second conformation the plurality of collecting fiber bundles are aligned the scanner assembly to provide an imaging end.

The details of one or more embodiments of the invention are set forth in the accompanying drawings and the description below. Other features, objects, and advantages of the invention will be apparent from the description and the drawings, and from the claims.

DETAILED DESCRIPTION

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention. It is further understood that any one or more of the following-described embodiments, examples, etc. can be combined with any one or more of the other following-described embodiments, examples, etc.

Figure 1:
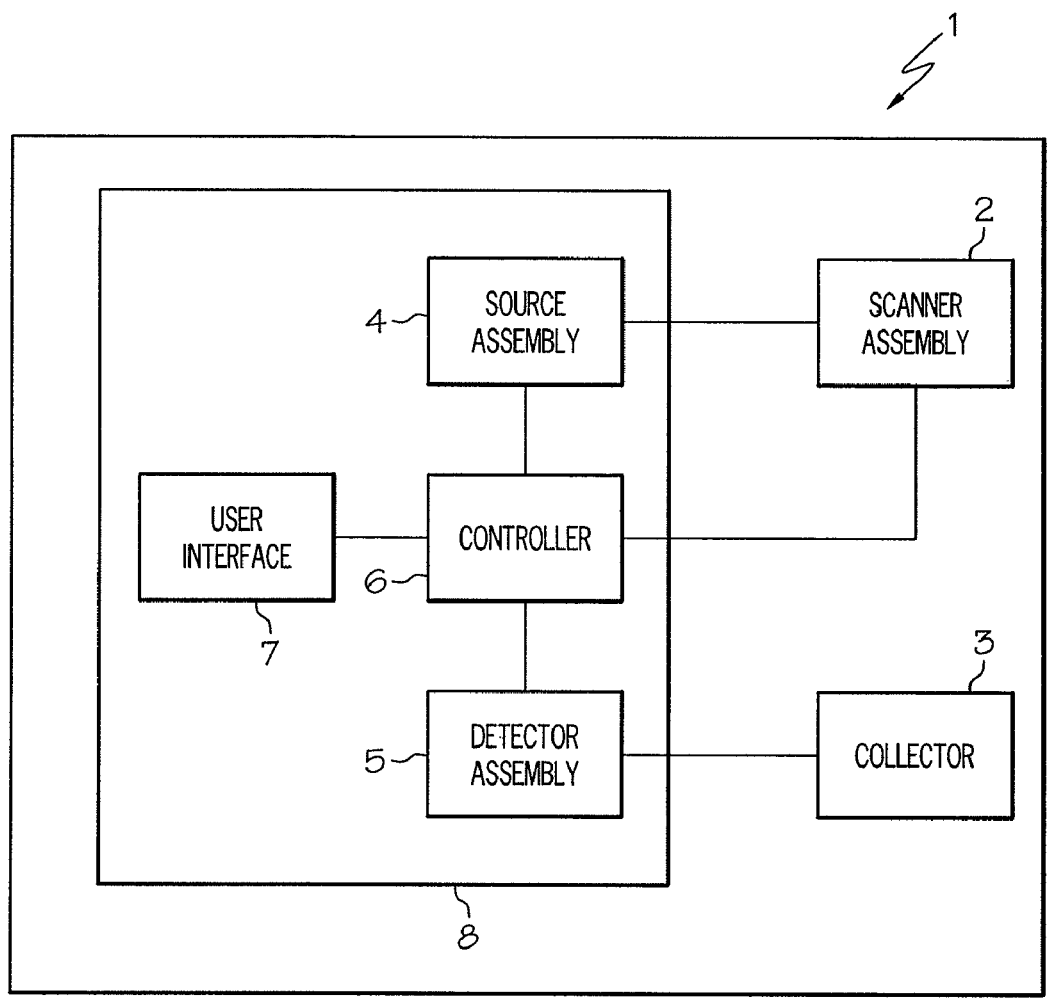
FIG. 1 is a block diagram of an embodiment of a medical device system including a scanner assembly.

Referring to FIG. 1, an embodiment of a scanning beam device 1, which may be part of a medical device, includes scanner assembly 2, collector 3, radiation source assembly 4, detector assembly 5, controller 6, and user interface 7. The radiation source assembly 4, detector assembly 5, controller 6 and user interface 7 make up functional element 8 that is known herein as a "console." The radiation source assembly 4, as selected by the user via the user interface 7, and acting through the controller 6, generates a wavelength of radiation (e.g., in the visible wavelength range and/or otherwise). This radiation is conveyed in a beam to scanner assembly 2, which causes the beam to be swept across an anatomical surface. The extent of this swept area is generally known as the "field of view" (FOV). Radiation returned from the scene (e.g., tissue, structures, and organs) within the FOV may be received by collector 3 and passed to detector assembly 5. The detector assembly converts the received radiation to electrical signals that are then processed by the controller to form an image on a display assembly, which in one embodiment may be included in user interface 7.

Figure 2:
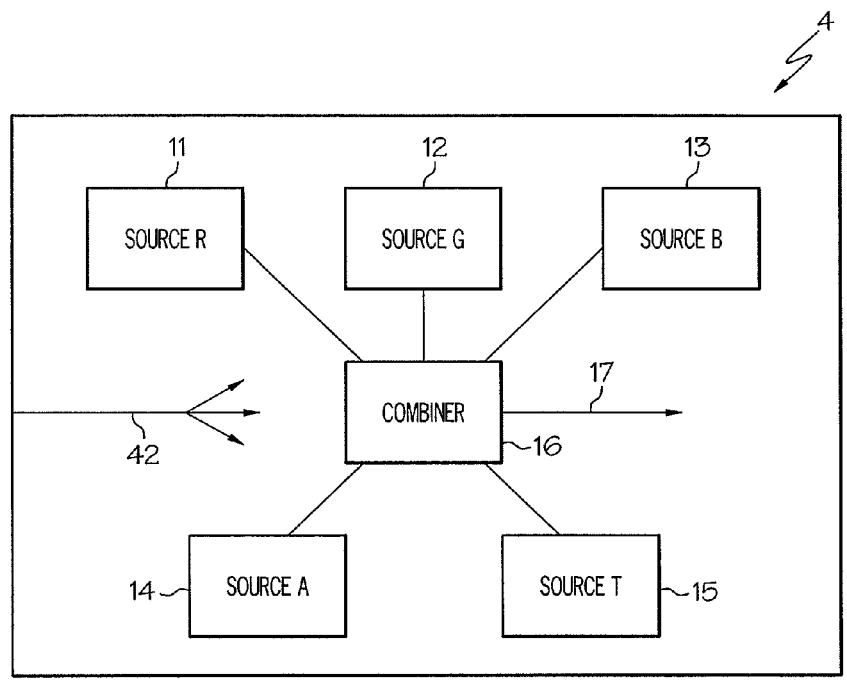
FIG. 2 is a block diagram of an embodiment of a source assembly including multiple sources for generating imaging, therapeutic and aiming beams.

FIG. 2 is a block diagram of one implementation of source assembly 4. Source assembly 4 includes multiple sources, each capable of generating radiation at a selected wavelength. Five sources are shown here, numbered 11 thru 15. It should be noted that while five sources are illustrated, there may be more or fewer sources depending, for example, on the end use. The outputs of the radiation sources 11-15, in some embodiments, may be brought together in combiner 16 to yield output beam 17. Combiner 16 may also include beam-shaping optics such as one or more collimating lenses and/or apertures. The sources may be of various types such as, but not limited thereto, light emitting diodes (LEDs), lasers, thermal sources, arc sources, fluorescent sources, gas discharge sources, or others. In some embodiments, sources 11, 12 and 13 comprise three lasers; a red diode laser, a green diode-pumped solid state (DPSS) laser, and a blue DPSS laser at approximately 635 nm, 532 nm, and 473 nm, respectively. Signals 42 may be provided by controller 6 (FIG. 1) to one or more of the sources and optionally combiner 16. Signals 42 may optionally control wavelength, power, modulation or other beam properties. The power of the beam may be modulated by a modulator, as taught in commonly assigned U.S. patent application Ser. No. 11/716,911, titled POWER MODULATION OF A SCANNING BEAM FOR IMAGING, THERAPY, AND/OR DIAGNOSIS, which is hereby incorporated by reference in its entirety.

The wavelength of radiation, for example, may be selected for imaging, therapy, or aiming. As used herein, an "imaging beam" refers to radiation selected for use in creating an image of a surface or region, a "therapeutic beam" refers to radiation selected to provide treatment of a condition such as diseased or damaged tissue, and an "aiming beam" refers to radiation selected to accentuate a portion of the FOV. In some embodiments, an additional source may provide a "diagnostic beam." A "diagnostic beam" as used herein refers to radiation selected for analysis or detection of a disease or other medical condition including, for example, to visualize the presence of (or to activate) a diagnostic marker. The diagnostic marker could be naturally occurring (e.g., auto or self fluorescence) or introduced as part of the diagnostic procedure (e.g., fluorescent dyes). The apparatus to operate such beams is disclosed in commonly assigned U.S. patent application Ser. No. 11/716,806, titled MEDICAL DEVICE INCLUDING SCANNED BEAM UNIT FOR IMAGING, THERAPY, AND/OR DIAGNOSIS, as well as the operation of treatment mapping or selecting a treatment path. This reference is hereby incorporated by reference in its entirety.

Figure 3:
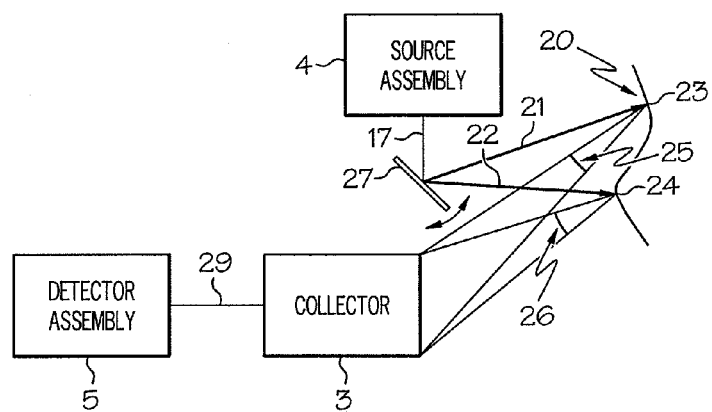
FIG. 3 is a block diagram illustrating radiation paths.

FIG. 3 illustrates the operation of device 1. Reflector 27, which is usually included in scanner assembly 2, receives a beam of radiation 17 from source assembly 4 and directs the beam onto surface 20, for example, for one or more of imaging, therapy, diagnostic, or aiming purposes. At one point in time, the beam deflected by reflector 27 is in the direction shown as 21, and impinges upon the surface to illuminate point 23. Reflector 27 oscillates in at least one axis (two axes in some embodiments), as indicated by the nearby arrowed arc, so that at some other point in time the deflected beam is in the direction indicated as 22 where, it illuminates point 24. Radiation is, in general, reflected, absorbed, scattered, refracted or otherwise affected by the properties of the surface. Radiation may leave the surface in many directions. Collector 3, however, may only receive that fraction of radiation which is returned from the surface and falls into the area subtended by its aperture. Regions 25 and 26 show the returned radiation that is captured by collector 3 when the beam is illuminating points 23 and 24 respectively. Directions 21 and 22 are not intended to represent any special part of the scan as the beam may be scanned using reflector 27 beyond them, and scans all points between them as well. Furthermore, a simplified two-dimensional view is represented by FIG. 3, and in general reflector 27 and collector 3 are adapted to illuminate and receive radiation from surfaces occupying space in three dimensions. Radiation returned from the FOV received by collector 3 is passed to detector assembly 5.

Some embodiments use a micro-electromechanical (MEMS) scanner reflector to direct the imaging, aiming and therapeutic beams onto the surface. MEMS scanner reflectors are described in, for example, U.S. Pat. No. 6,140,979, entitled SCANNED DISPLAY WITH PINCH, TIMING, AND DISTORTION CORRECTION; U.S. Pat. No. 6,245,590, entitled FREQUENCY TUNABLE RESONANT SCANNER AND METHOD OF MAKING; U.S. Pat. No. 6,285,489, entitled FREQUENCY TUNABLE RESONANT SCANNER WITH AUXILIARY ARMS; U.S. Pat. No. 6,331,909, entitled FREQUENCY TUNABLE RESONANT SCANNER; U.S. Pat. No. 6,362,912, entitled SCANNED IMAGING APPARATUS WITH SWITCHED FEEDS; U.S. Pat. No. 6,384,406, entitled ACTIVE TUNING OF A TORSIONAL RESONANT STRUCTURE; U.S. Pat. No. 6,433,907, entitled SCANNED DISPLAY WITH PLURALITY OF SCANNING ASSEMBLIES; U.S. Pat. No. 6,512,622, entitled ACTIVE TUNING OF A TORSIONAL RESONANT STRUCTURE; U.S. Pat. No. 6,515,278, entitled FREQUENCY TUNABLE RESONANT SCANNER AND METHOD OF MAKING; U.S. Pat. No. 6,515,781, entitled SCANNED IMAGING APPARATUS WITH SWITCHED FEEDS; U.S. Pat. No. 6,525,310, entitled FREQUENCY TUNABLE RESONANT SCANNER; and U.S. patent application Ser. No. 10/873,540, entitled SCANNING ENDOSCOPE; all of which are hereby incorporated by reference in their entirety.

Figure 4:
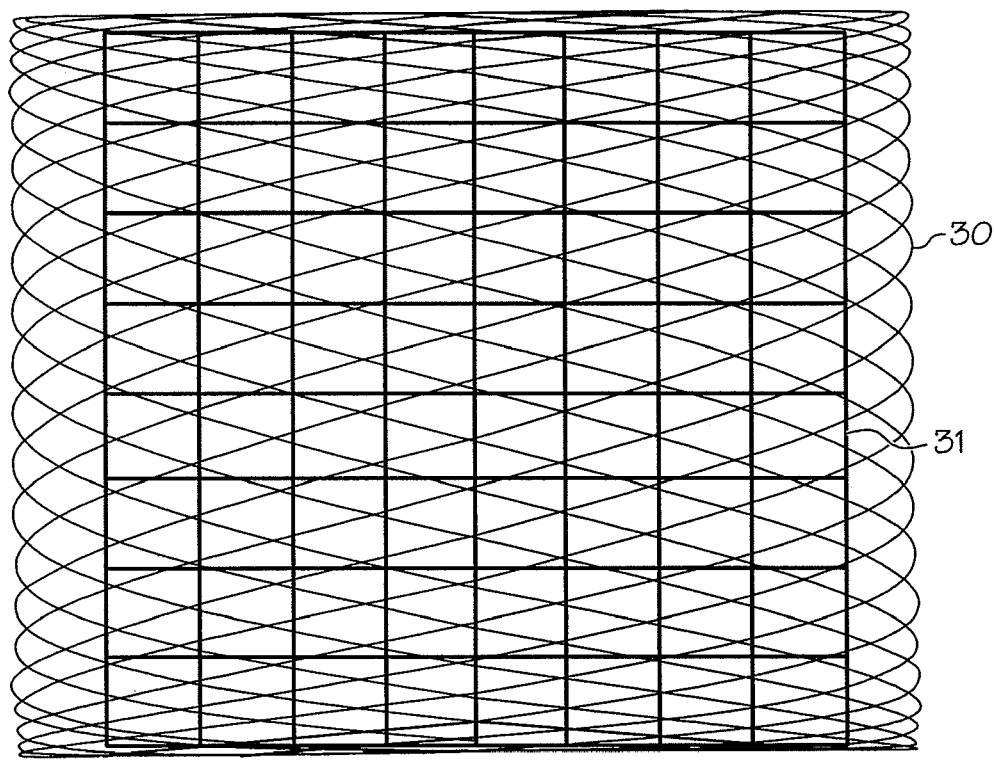
FIG. 4 is an illustration of a bi-sinusoidal scan pattern and a rectangular coordinate pattern plotted together.

Referring now to FIG. 4, in one embodiment, reflector 27 scans the beam of radiation in a pattern shown as an idealized bi-resonant or bi-sinusoidal scan pattern. High-speed MEMS reflectors and other resonant deflectors as described herein are configured and driven to execute sinusoidal angular deflections in two orthogonal axes, yielding the Lissajous pattern shown in FIG. 4. Most current display devices are configured to address display data in a Cartesian form, for example as row and column, or a particular pixel along a nearly-horizontal scan line. The bi-resonant or Lissajous scan path 30 is shown overlaid with the Cartesian or rectilinear grid 31. In the illustrated instance, the intersections between the vertical and horizontal lines of the Cartesian grid 30 represent display pixel positions while the Lissajous trace 31 represents the actual path taken by the scanned spot. As the actual scan path does not align perfectly with all the rectilinear pixel positions, these image values may be determined through interpolation. In some embodiments, registration of the Lissajous trace 30 to the Cartesian grid 31 is based on a marker that links a reference point in the scan to a point in the rectilinear matrix.

Figure 5:
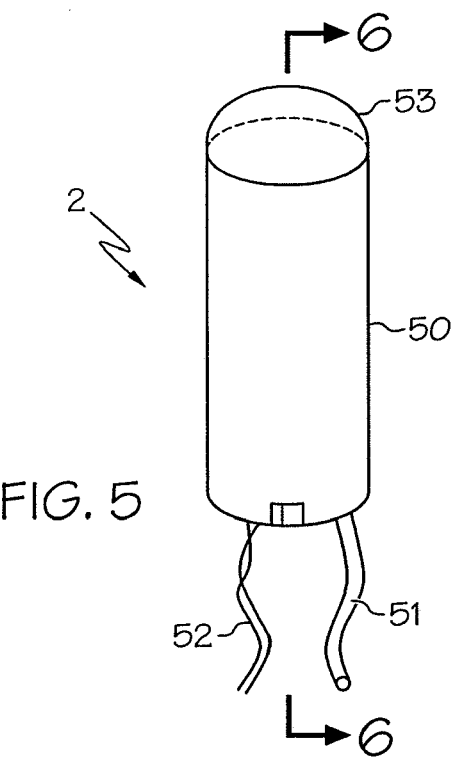
FIG. 5 is a perspective view of an embodiment of a scanner assembly.

FIG. 5 is an external view of one embodiment of the scanner assembly 2. Scanner assembly 2 includes a housing 50 that encloses the reflector 27 and other components. A source fiber 51 is used to deliver radiation from the source assembly 4 to the scanner assembly 2. Source fiber 51 may be a single mode optical fiber. In some embodiments, one or more fibers may be used to deliver imaging beams and one or more other fibers may be used to deliver a therapeutic beam (e.g., therapeutic beams having longer wavelengths, e.g., greater than 1700 nm and/or higher power). In certain embodiments, a different type of fiber, such as a holey fiber, may be used to transmit energy from the source assembly 4. In some embodiments, the same optical fiber 51 is used to deliver both the imaging beams and the therapeutic beams to the reflector, the optical fiber defining a common path for both types of beams.

Electrical wires 52 convey drive signals for the reflector 27 and other signals (position feedback, temperature, etc.) to and from controller 6 (FIG. 1). Wires 52 may also provide control and feedback connections for controlling focus characteristics of the beam shaping optic 56. In one embodiment, source fiber 51, electrical wires 52 and any other fibers or wires connected to scanner assembly 2 may be bound together into a cable (shown as 76 in FIG. 8). In one embodiment, the distal end of the scanner assembly 2 may be fitted with an optical element 53 which allows the scanned beam to illuminate the FOV. This element 53 is generally referred to and illustrated as a dome; however, its curvature, contour, and surface treatments may depend on the application and optical properties required. In some embodiments, dome 53 provides a hermetic seal with the housing 50 to protect the internal elements from the environment.

Figure 6:
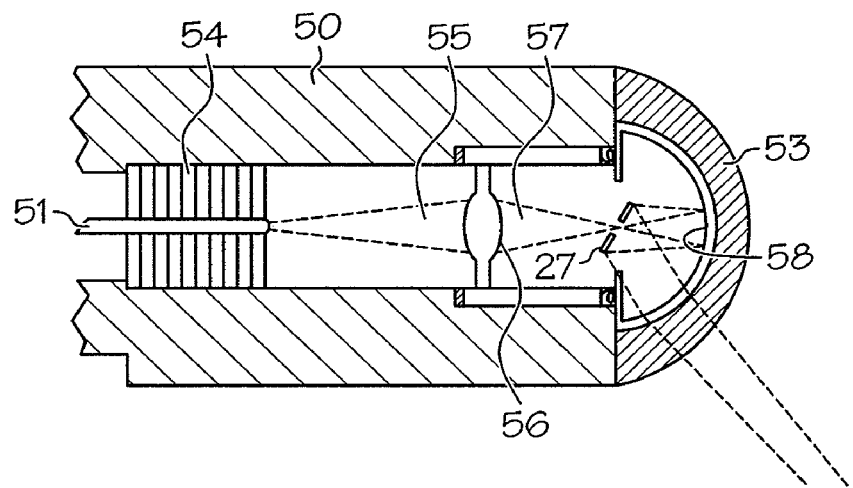
FIG. 6 is a side, section view of the scanner assembly of FIG. 5 along line 6-6.

FIG. 6 shows one embodiment for the internal components of scanner assembly 2. Source fiber 51 is affixed to the housing 50 by ferrule 54. The end of the source fiber 51 may be polished to create a beam 55 of known divergence. The beam 55 may be shaped by a beam shaping optic or lens 56 to create a beam shape appropriate for transmission through the system. After shaping, shaped beam 57 is fed through an aperture in the center of reflector 27, then reflected off a first reflecting surface 58. First reflecting surface 58 may have a beam shaping function. Beam 57 is then directed onto reflector 27 and then out of scanner assembly 2, the details of which (in the case of an imaging beam) are described in U.S. patent application Ser. No. 10/873,540, entitled SCANNING ENDOSCOPE, the details of which are hereby incorporated by reference as if fully set forth herein. Any suitable materials can be used to form reflector 27. In some embodiments, the reflective surface of reflector 27 may be formed of gold or other suitable material for directing each of the beams including relative high energy therapeutic radiation. In other embodiments, a multilayer dielectric configuration may be used in forming reflector 27.

In one embodiment, scanning beam device 1 may include a zoom mechanism. The zoom mechanism may operate by adjusting the scan of the oscillating reflector included in scanner assembly 2. In one embodiment, the zoom mechanism adjusts the scan by reducing the frequency of the scan to collect more data within each specified area, e.g., a pixel, of the FOV. In another embodiment, the zoom mechanism adjusts the scan by reducing the area the scanner sweeps across within the FOV, which allows the collection of more data within the reduced area. In this way, scanner assembly 2 does not need to be physically moved nearer or farther from the FOV to get a larger or smaller image.

Scanner assembly 2 may be about 2 to about 4 millimeters by about 4 to about 10 millimeters, or any other suitable dimension. Scanner assembly 2 may by cylindrical, rectangular, or any other configuration that can be inserted into the body, or made part of an introducer. Scanner assembly 2 may be capable of being deployed within the anatomy. In one embodiment, scanner assembly 2 may enter the anatomy through a natural orifice (i.e. the mouth, nasal passage, anus, urethra, ureter, etc.) for a less invasive procedure.

Figure 7:
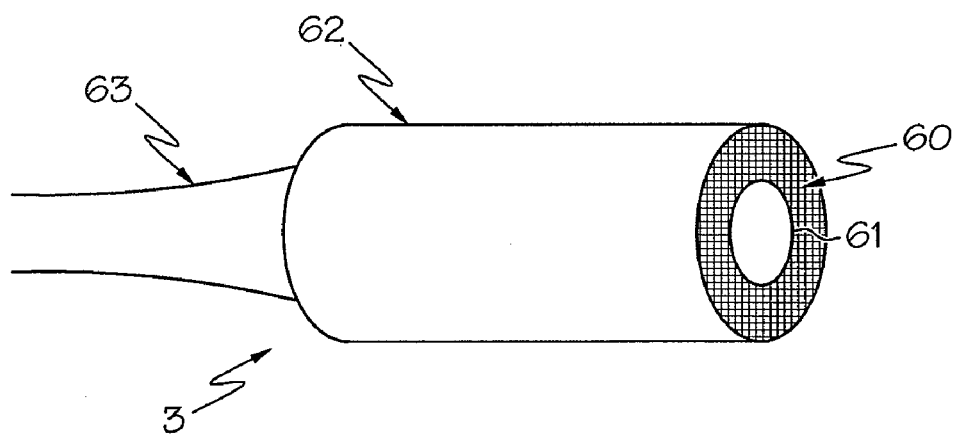
FIG. 7 is a perspective view of an embodiment of a collector.

In another embodiment, as shown in FIG. 7, collector 3 may include face 60, central void 61, housing 62, and collecting fibers 63. Radiation reflected from the FOV impinges on the face 60 of collector 3, which constitutes the receiving aperture. Face 60 may be made up of the polished ends of a large number of small diameter, multimode collecting fibers 63 which conduct the radiation to detector assembly 5 (FIGS. 1 and 3). In one embodiment, scanner assembly 2 is inserted into central void 61 of housing 62 to form a module 70 that has a cable to connect the module 70 to the console 8 of scanning beam device 1. The cable may include the bundle of collecting fibers, the source fiber, and any other wiring for controlling scanner assembly 2 and collector 3. The fiber ends making up face 60 may be formed in a plane, or into other geometries to control the pattern of receiving sensitivity. They may be coated with diffusing or other materials to improve their angle of acceptance, to provide wavelength conversion, or wavelength selectivity. In one embodiment, detector assembly 5 may be configured to form the receiving aperture and mounted in position to receive the reflected radiation directly, without the need for a separate collector 3.

Figure 8A:
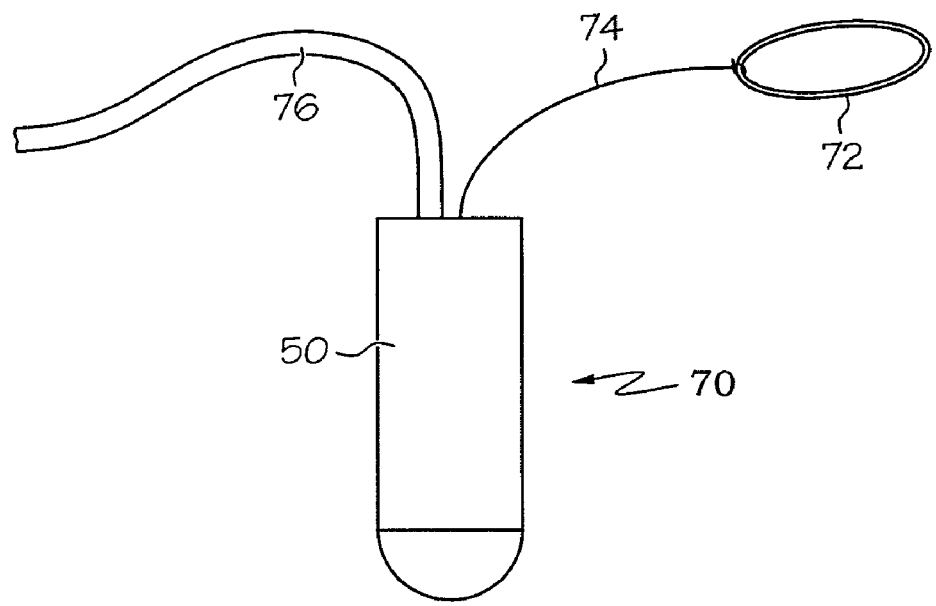
FIG. 8A is a side view of a scanner assembly including a connecting structure.

Module 70 may include a connecting structure. Referring to FIG. 8A, the connecting structure illustrated is a suture loop 72. Suture loop 72 may be used to secure module 70 to an anatomical structure to scan the FOV from the secured position. Suture loop 72 is attached to housing 50 by tether 74 (e.g., formed of an absorbable or non-absorbable material). Tether 74 may be formed of any suitable material such as a polymer, Nitinol or other metal, or textile materials. Module 70 may include cable 76 to connect the module 70 to console 8 of scanning beam device 1. In another embodiment, module 70 may include collector 3 within housing 50 or in an embodiment similar to that shown in FIG. 7.

Figure 8B:
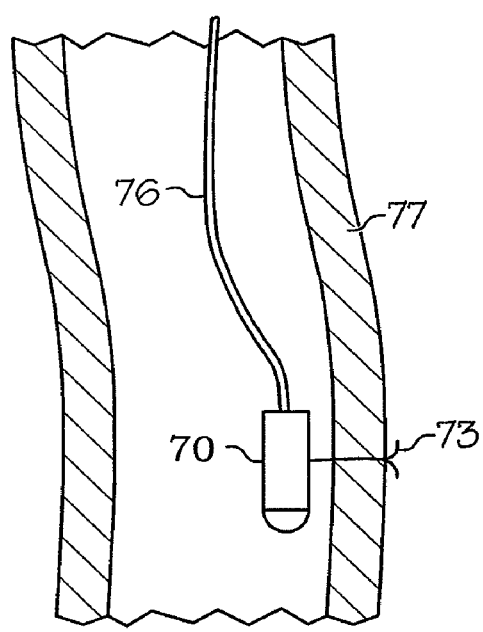
FIGS. 8B, 8C are side views of a scanner assembly including a anchor type connecting structure.
Figure 8C:
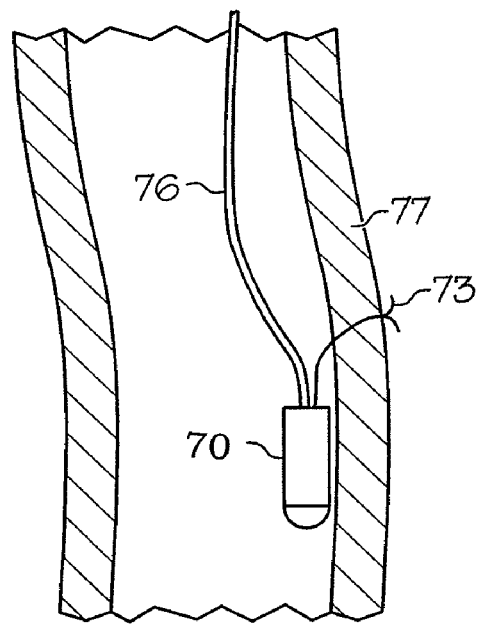

In another embodiment module 70 includes, as shown in FIGS. 8B and 8C, an anchor 73 as the connecting structure. The anchor 73 is introduced into the tissue of the anatomical structure 77 or a bone and is retained using methods known in the art, such as but not limited to the Mitek soft tissue anchor and Mitek bone anchor by DePuy Mitek, Inc. a Johnson & Johnson Company. Anchors used in hernia procedures are taught in commonly assigned U.S. Pat. Nos. 6,447,524 FASTENER FOR HERNIA FIXATION and 6,425,900 METHOD FOR ATTACHING HERNIA MESH, which are hereby incorporated by reference in their entirety. The fasteners disclosed for the hernia procedures may be applicable for use in procedures in other anatomical structures as disclosed herein. The anchor may be comprised of a material such as Nitinol or a polymer material. Upon completion of the procedure, the anchor may be removed. Alternatively, the anchor may be comprised of bioabsorbable materials, in which case the scanner may be disconnected from the anchor for removal.

Figure 9:
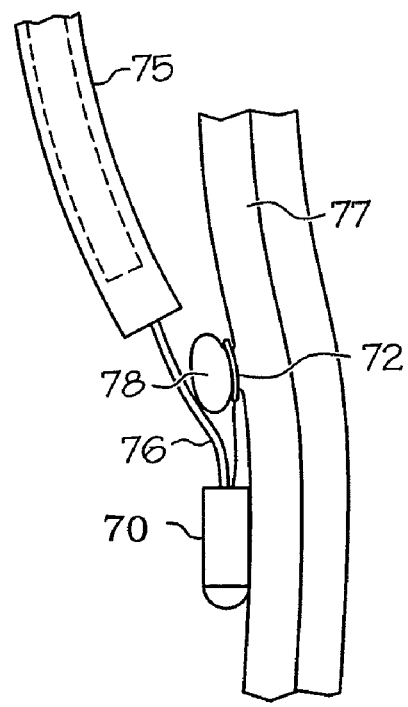
FIG. 9 illustrates the scanner assembly of FIG. 8A secured to an anatomical structure.

FIG. 9 illustrates module 70 secured to an anatomical structure 77 within a patient's body using suture loop 72. Anatomical structure 77 may be any portion of the body. Suture loop 72 may be used to secure module 70 to or within tissue, a lumen wall, a cavity wall, or the surface of an internal organ or structure. Suture loop 72 secures module 70 at a position within the body chosen by a clinician to image a portion of the anatomy. As shown, suture loop 72 is looped around a protuberance 78 of the anatomical structure 77. An introducer 75 may be used to place module 70 within the body. Introducer 75 may be a needle, trocar, endoscope or other medical scope, a grasper, a surgical tool, a cutting tool, or any other medical instrument that is capable of delivering module 70 to the chosen position.

Figure 10:
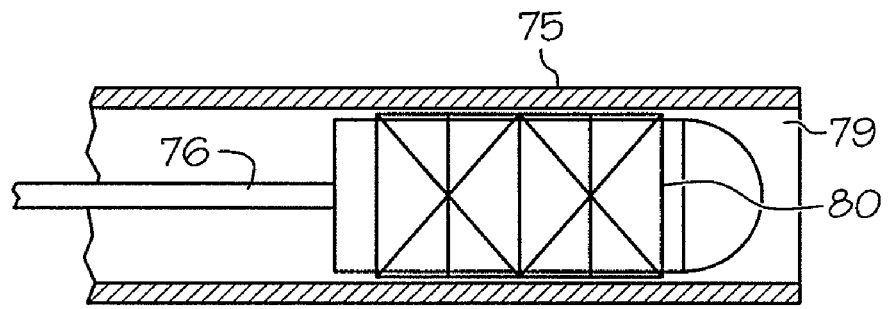
FIG. 10 is a side view of a scanner assembly including an expandable connecting structure that is within an introducer.
Figure 11:
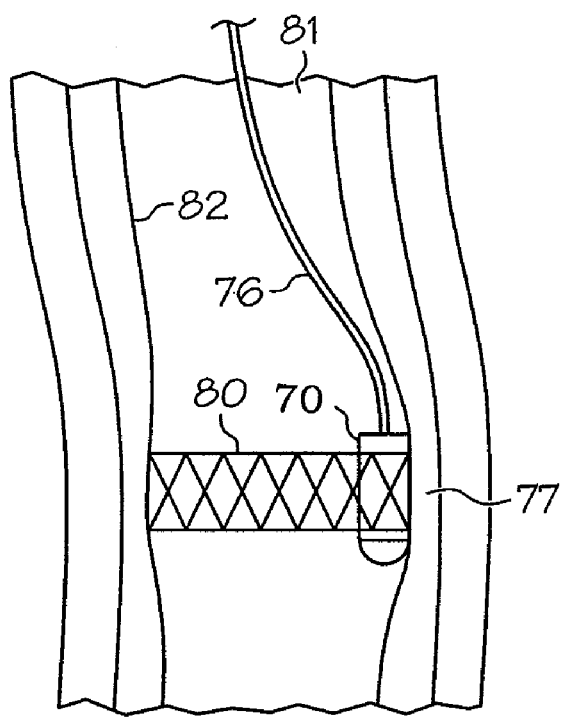
FIG. 11 illustrates the scanner assembly of FIG. 10 secured to an anatomical structure.

In another embodiment, shown by FIGS. 10 and 11, module 70 includes stent-like, expandable connecting structure 80 (e.g., formed of metal, silicone or a hybrid material) for securing module 70 in an anatomical structure 77. FIG. 10 shows connecting structure 80 in a collapsed configuration inside a channel 79 of introducer 75 for delivery to an imaging location. Referring to FIG. 11, after module 70 is delivered to the imaging location by introducer 75, module 70 is removed from channel 79 and connecting structure 80 is expanded into contact with the surrounding anatomical structure 77. In one embodiment, the anatomical structure is lumen 81. Module 70 may be placed near to the lumen wall 82 so as to place module 70 away from the center of lumen 81 to facilitate passage of fluid thereby. Expandable connecting structure 80 may be self-expanding (e.g., outwardly biased or formed of a memory shape material). In another embodiment, expandable connecting structure 80 may be expanded by a balloon, for example but not limited thereto.

Figure 12:
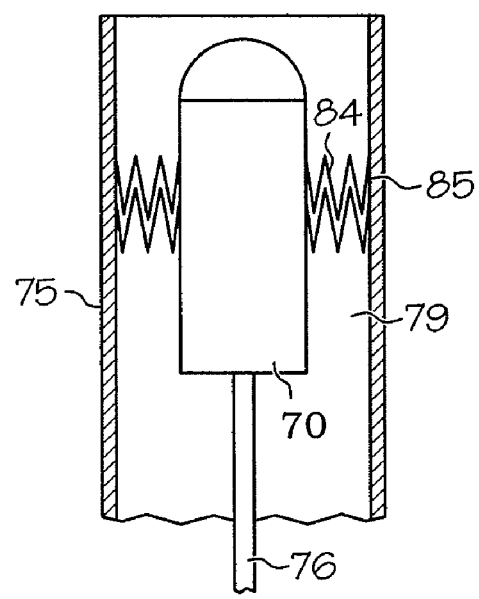
FIG. 12 is a side view of a scanner assembly including an expandable connecting structure having a barb that is within an introducer.
Figure 13:
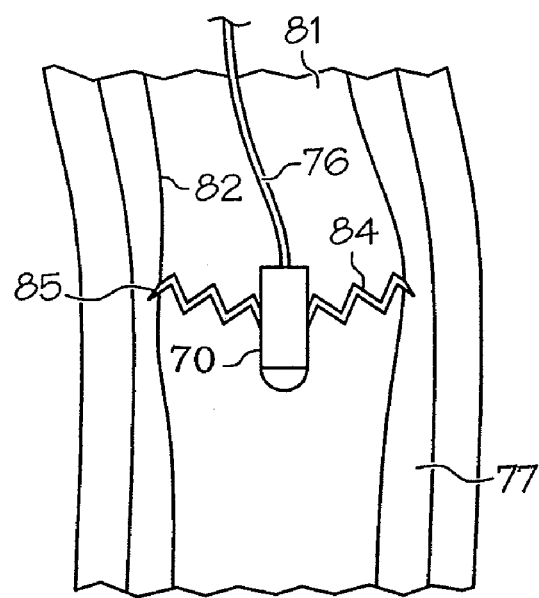
FIG. 13 illustrates the scanner assembly of FIG. 12 secured to an anatomical structure.

FIGS. 12 and 13 illustrate another embodiment of module 70 including expandable connecting structure 84 with barbs 85 for use in securing module 70 to an anatomical structure 77. FIG. 12 shows connecting structure 84 in a collapsed configuration inside channel 79 of introducer 75 for delivery to an imaging location. Referring to FIG. 13, after module 70 is delivered to the imaging location by introducer 75, module 70 is removed from channel 79 and connecting structure 84 is expanded into contact with the surrounding anatomical structure 77, as shown with barbs 85 penetrating anatomical structure 77 to secure module 70 thereto. FIG. 13 illustrated module 70 secured within lumen 81 by barbs 85 penetrating the lumen wall 85.

Other connecting structures for securing module 70 at an imaging location within the anatomy include, but are not limited to, a magnet, a clamp, a biocompatible adhesive material, a counterweight, or tension on cable 76. In some instances, module 70 may be located at the imaging location using the anatomy itself without any need for connecting structure or material. In some embodiments, module 70 may be attached to an introducer or other medical instrument inserted into the anatomy at a fixed location, such as a trocar or needle.

Figure 14:
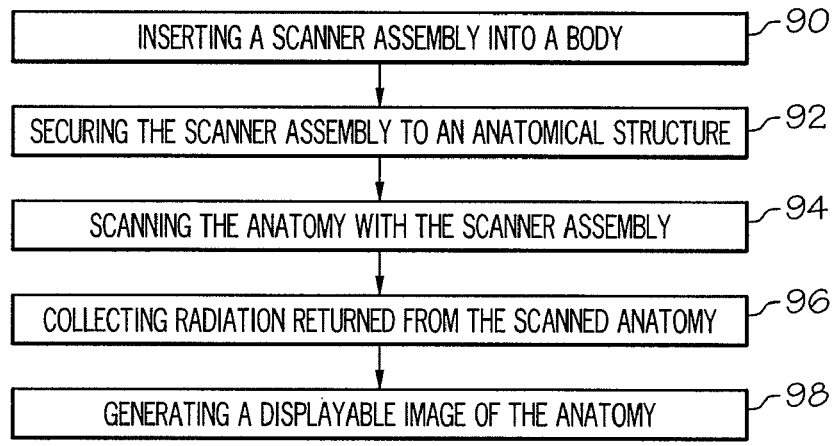
FIG. 14 is a flow chart of a method for viewing a portion of a patient's internal anatomy.

Referring now to FIG. 14, a method for viewing a portion of a patient's anatomy is illustrated. The method includes the steps of placing a scanner assembly 2 including an oscillating reflector into the anatomy 90, securing the scanner assembly 2 to an anatomical structure 92, scanning the anatomy with the scanner assembly 94, collecting radiation returned from the scanned anatomy 96, and generating a displayable image of the anatomy 98. The displayable image may be displayed on a display system that may be included as a component of the scanning beam device 1. In another embodiment, the method may include the step of removing the scanner assembly 2 when the need for the scanner assembly 2 to be secured to the anatomical structure is over. In the illustrated embodiments below, because scanner assembly 2 is quite small, the assembly 2 may only extend minimally off the anatomical structure it is secured to. In the embodiments below for FIGS. 15 and 16 the scanner assembly 2 may be combined with a collector 3 in a module 70 to be placed into the anatomy.

Figure 15:
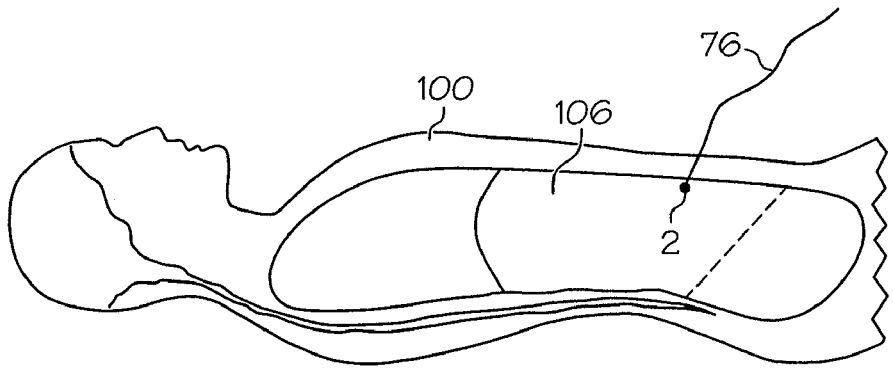
FIG. 15 is a side section view of a body with a scanning module inserted therein.

As shown in FIG. 15, scanner assembly 2 may be inserted percutaneously into the abdomen 106 or any other location within body 100. Scanner assembly 2 includes reflector 27, as shown in FIGS. 3 and 6, that oscillates to scan a beam of radiation across the anatomy. Scanner assembly 2 may have zoom capabilities provided by a zoom mechanism that may be a component of scanning beam device 1. In one embodiment, scanner assembly 2 may be inserted into a body cavity at a point to provide a central viewpoint of the cavity. In the abdomen 106, the umbilicus may be a point of insertion that provides the central viewpoint.

Inserting scanner assembly 2 may be by any medical procedure or instrument that is capable of placing the scanner assembly 2 at the desired anatomical structure. The insertion may be, but is not limited to, the scanner assembly 2 itself having a penetrating tip, a trocar or needle containing or capable of deploying the scanner assembly 2, an endoscope or other medical instrument carrying scanner assembly 2 in a working channel from which the assembly may be deployed, a surgical tool that carries scanner assembly 2 through an open incision, or placement of scanner assembly 2 through a natural or non-natural opening in the body with or without using an introducer.

The insertion of scanner assembly 2 may be in any location within the anatomy. Scanner assembly 2 may be, but is not limited to, placement within a lumen, a body cavity, an organ, and/or tissue. A few specific examples include, but are not limited to, the colon, the uterus, the prostate, the esophagus, the stomach, the intestines, the abdomen, the thoracic cavity, the blood vessels, and the heart. Scanner assembly insertion is also described in U.S. application Ser. No. 11/651,255, filed Jan. 9, 2007, entitled METHOD OF IN VIVO MONITORING USING AN IMAGING SYSTEM INCLUDING SCANNED BEAM IMAGING UNIT, the details of which are hereby incorporated by reference.

Figure 16:
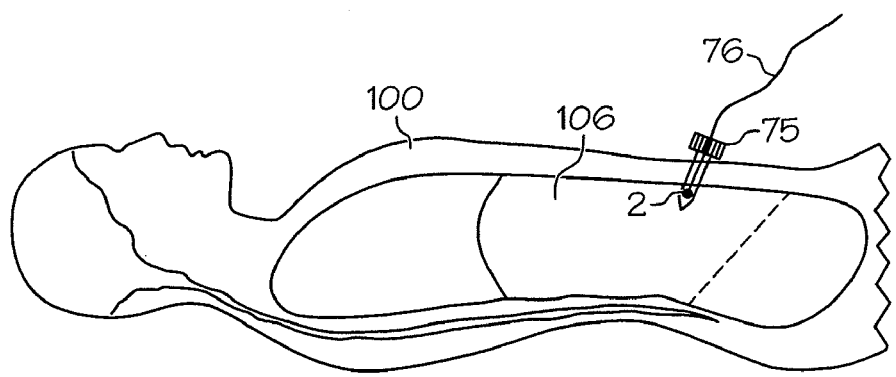
FIG. 16 is a side section view of a body with an introducer including a scanning module inserted therein.

In another embodiment, as shown in FIG. 16, an introducer 75 may be used to insert scanner assembly 2 including cable 76 into body 100 within the abdomen 106. Introducer 75 may have a penetrating tip. The penetrating tip may be used to penetrate percutaneously into body 100. The introducer may have scanner assembly 2 built into the penetrating tip or body of the introducer, or the introducer may have an open channel through which scanner assembly 2 may be fed into body 100. The introducer from which scanner assembly 2 is fed into the body may be removed or may remain in the body. The introducer may be a needle, a trocar, or any other medical instrument capable of introducing the scanner assembly 2 into the body. In one embodiment, cable 76 may be used to feed scanner assembly 2 through the open channel within the introducer, and may be used to push scanner assembly 2 out of the channel into the body. In another embodiment a rod may be pushed through the channel and used to push scanner assembly 2 into the body.

Securing the scanner assembly 2 to an anatomical structure within the body may be by any means that will hold scanner assembly 2 in place. The advantage is that the clinician does not have to continue to hold scanner assembly 2 in place or move it during the procedure. Scanner assembly 2 may be moved if the clinician desires, but ideally once scanner assembly 2 is in place, it stays in place during the procedure. Scanner assembly 2 may be held in place against an anatomical structure by pulling cable 76 until the assembly is against the anatomical structure. In one embodiment, a counterweight may be applied to cable 76 to pull the assembly against the structure. In another embodiment, a removable adhesive may be coated onto scanner assembly 2 to adhere the assembly to the anatomical structure. In another embodiment, scanner assembly 2 may include a connecting structure. The connecting structure may be a suture loop 72, as illustrated in FIGS. 8 and 9, to suspend scanner assembly 2 from tissue or protuberances within the body. In yet other embodiments, as illustrated in FIGS. 10 to 13, the connecting structure may be expandable, and may include barbs. In another embodiment, the connecting structure may be a magnet and/or a clamp.

Figure 17:
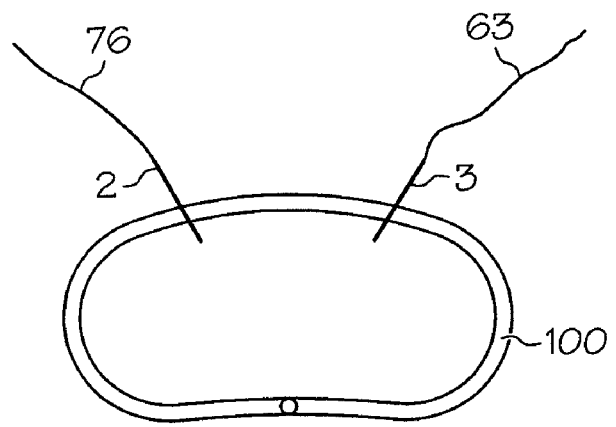
FIG. 17 is a cross-sectional view of the body including a separate scanner assembly and collector.

In another embodiment, as illustrated in FIG. 17, the method for viewing a portion of a patient's anatomy further includes the step of inserting collector 3 having collecting fibers 63 into body 100 at a location removed from the insertion point of scanner assembly 2 having cable 76. Cable 76 and collecting fibers 63 may be adapted to connect to a component of scanning beam device 1. Scanner assembly 2 and collector 3 may each be equipped with a pointed or penetrating element to facilitate insertion percutaneously into the anatomy. In another embodiment, scanner assembly 2 and collector 3 may each be part of separate introducers that may be inserted into the anatomy. The introducer may be any of the introducers explained above.

Figure 18A:
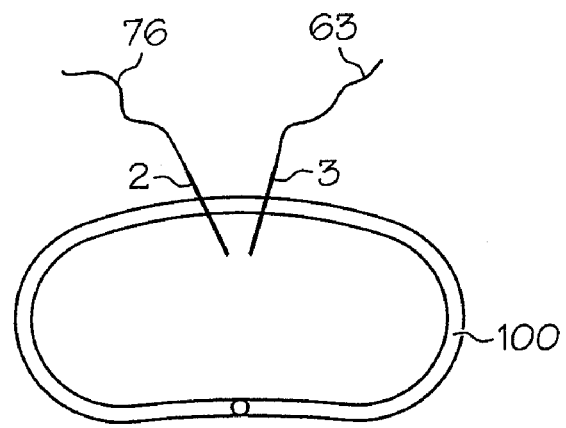
FIGS. 18A and 18B are cross-sectional views of a body illustrating the separate insertion of a scanner assembly and a collector that after insertion are magnetically coupled.
Figure 18B:
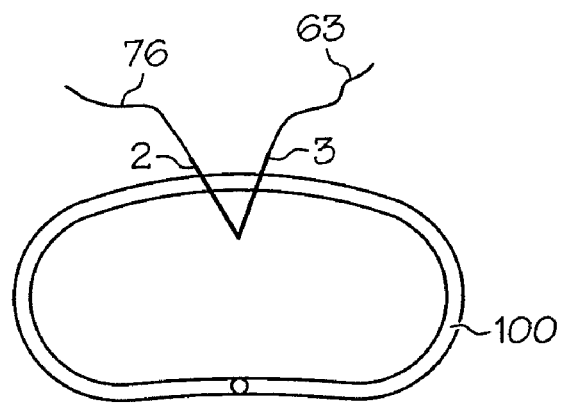

Referring now to FIGS. 18A and 18B, scanner assembly 2 and collector 3 may each include a magnet. The magnets included in scanner assembly 2 and collector 3 are of opposite polarity. Scanner assembly 2 and collector 3 are inserted separately into body 100, yet in close enough proximity to one another that the magnets in scanner assembly 2 and collector 3 are attracted to one another to magnetically couple scanner assembly 2 and collector 3. FIG. 18A illustrates the insertion of scanner assembly 2 and collector 3 in close enough proximity for the magnets to attract. FIG. 18B illustrates scanner assembly 2 and collector 3 magnetically coupled together after insertion into body 100. Scanner assembly 2 and collector 3 may be within a flexible housing to enable the movement or bending of scanner assembly 2 and collector 3 when the magnetic attraction pulls them together. In another embodiment, collector 3 and scanner assembly 2 may be mechanically coupled together, for example, by a clasp, a latch, tooth and hook fabric, or the like.

In another embodiment, scanner assembly 2 may be coupled with a collector 3 in a module and inserted into the anatomy. Another collector 3 may also be inserted into the anatomy at a location removed from the module. The separate collector 3 may provide a secondary nuanced view of the scanned anatomy. The secondary nuanced image of the anatomy is of the same portion of the anatomy, but the image may have varied shading, obscuration, glints, or color changes that may indicate useful information about the anatomy to the clinician.

Figure 19A:
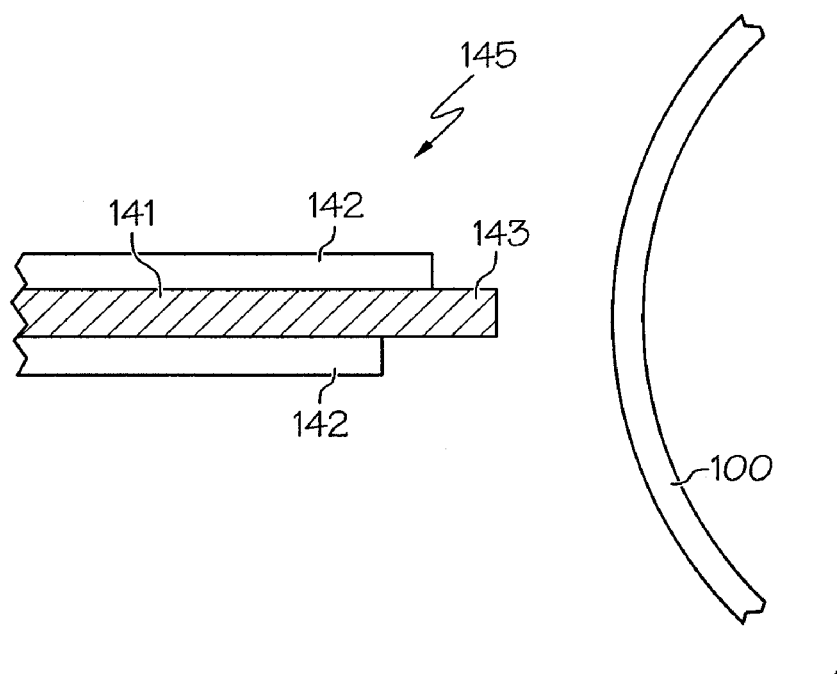
FIGS. 19A and 19B are perspective views of an adjustable combined scanner assembly and collector.
Figure 19B:
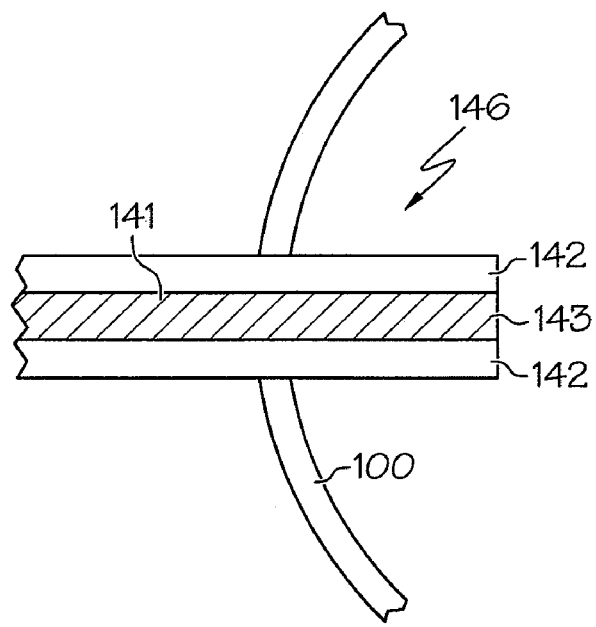

Referring now to FIGS. 19A and 19B, a scanner assembly 141 and a collector as a plurality of collecting fiber bundles 142 may convert from a first conformation 145 to facilitate insertion into the body 100 or the anatomy and a second conformation 146 to facilitate imaging the anatomy. In the first conformation 145 a central scanner assembly 141 having an insertion end 143 has a plurality of collecting fiber bundles 142 around its periphery. The collecting fiber bundles 142 may be longitudinally staggered around the scanner assembly 141. The collecting fiber bundles 142 may be movable such that the fiber bundles 142 can change to the second conformation 146. Scanner assembly 141 may include any of the features described above for scanner assembly 2. The first conformation 145 may be inserted percutaneously into the body. After insertion the collecting fibers bundles 142 may be moved forward toward the insertion end 143 of the scanner assembly 141 to form the second conformation 146.

In the above description and drawings certain embodiments were disclosed, however, it will be apparent that variations and modifications of the embodiments may be made without departing from the principles of the invention or the scope of the appended claims. Accordingly, other embodiments are within the scope of the following claims.

What is claimed is:

1. A scanner assembly and a collector that converts from a first conformation to facilitate percutaneous insertion into a patient's anatomy and a second conformation to facilitate imaging a portion of the anatomy after the percutaneous insertion comprising:

a scanner assembly that scans radiation from a radiation source across a portion of the anatomy, the scanner assembly having an insertion end; and a plurality of collecting fiber bundles that receive radiation returned from the portion of the anatomy, collecting fiber bundles being arranged around the periphery of the scanner assembly, wherein each of the collecting fiber bundles are longitudinally staggered a distance away from the insertion end of the scanner and are staggered relative to one another in the first conformation such that the combination of the plurality of collecting fiber bundles and the scanner assembly provides a pointed end for percutaneously inserting the scanner assembly and the collecting fiber bundles into the anatomy and in the second conformation the plurality of collecting fiber bundles were moved through the distance to place an end of each of the collecting fiber bundles into alignment with the insertion end of the scanner assembly to provide an imaging end.

2. The combined scanner assembly and collector of claim 1 wherein the scanner assembly includes an oscillating reflector.

* * * * *